United States Patent
Sushkevich et al.

(10) Patent No.: US 11,136,276 B2
(45) Date of Patent: Oct. 5, 2021

(54) SINGLE-STAGE METHOD OF BUTADIENE PRODUCTION

(71) Applicant: LLC "ETB CATALYTIC TECHNOLOGIES", Moscow (RU)

(72) Inventors: Vitaly Leonidovich Sushkevich, Minsk (BY); Andrey Valentinovich Smirnov, Moscow (RU); Irina Igorevna Ivanova, Moscow (RU)

(*) Notice: Subject to any disclaimer, the term of this patent is extended or adjusted under 35 U.S.C. 154(b) by 178 days.

(21) Appl. No.: 16/305,056

(22) PCT Filed: Jul. 7, 2017

(86) PCT No.: PCT/RU2017/000505
§ 371 (c)(1),
(2) Date: Nov. 28, 2018

(87) PCT Pub. No.: WO2018/182450
PCT Pub. Date: Oct. 4, 2018

(65) Prior Publication Data
US 2020/0317589 A1 Oct. 8, 2020

(30) Foreign Application Priority Data
Mar. 31, 2017 (RU) ................................ 2017110879

(51) Int. Cl.
*C07C 1/20* (2006.01)
*C07C 11/167* (2006.01)

(52) U.S. Cl.
CPC .............. *C07C 1/20* (2013.01); *C07C 11/167* (2013.01); *C07C 2529/74* (2013.01); *C07C 2529/76* (2013.01)

(58) Field of Classification Search
CPC ...... C07C 11/167; C07C 1/20; C07C 2529/74; C07C 2529/76; B01J 21/06; B01J 29/74; B01J 29/76
See application file for complete search history.

(56) References Cited

U.S. PATENT DOCUMENTS

2017/0226028 A1* 8/2017 Smith .................. C08F 236/08

FOREIGN PATENT DOCUMENTS

RU          2440962 C1          1/2012

OTHER PUBLICATIONS

VL Sushkevich, II Ivanova, E Taarning, Ethanol conversion 5 into butadiene over Zr-containing molecular sieves doped with silver, Green Chemistry, 17 (2015) 2552-2559.
Sushkevich VL, the thesis work, AVTOREFERAT, Moscow, Sep. 27, 2013.

* cited by examiner

*Primary Examiner* — Sharon Pregler
(74) *Attorney, Agent, or Firm* — Nixon & Vanderhye PC

(57) ABSTRACT

The invention relates to a gas-phase synthesis of butadiene from ethanol or from a mixture of ethanol and acetaldehyde. The method of production includes conversion of ethanol or a mixture of ethanol with acetaldehyde in the presence of a catalyst, wherein the reaction is carried out in the presence of a solid catalyst with a mesoporous Zr-containing zeolite having a BEA type structure and at least one metal in a zero oxidation state selected from the group: silver, copper and gold. The claimed method is suitable for carrying out the reaction under continuous flow conditions in the reactor with a fixed bed of catalyst. The invention makes possible to achieve a high yield of butadiene with high selectivity to butadiene and high stability of the catalyst.

7 Claims, No Drawings

SINGLE-STAGE METHOD OF BUTADIENE PRODUCTION

FIELD OF THE INVENTION

The invention belongs to the field of chemical industry and is intended for production of monomer-butadiene.

BACKGROUND OF THE INVENTION

Butadiene is used mainly as a monomer in the synthesis of synthetic rubbers like polybutadiene, butadiene-nitrile rubber, butadiene-styrene rubber, etc.

Currently, there are two main methods to produce butadiene in industry. First is butadiene isolation from the products of pyrolysis of oil. Second represents butadiene synthesis via one- or two-stage catalytic dehydrogenation of normal butane and butenes of oil processing gases and associated gases. However, due to the rise in oil prices, technologies for production of butadiene from ethanol provoke interest.

Historically, the first methods for production of butadiene from ethanol are processes consisting of two stages: the dehydrogenation of ethanol to acetaldehyde with the subsequent conversion of a mixture of acetaldehyde and ethanol to butadiene. Copper-based catalysts are used at the dehydrogenation stage, and tantalum or magnesium oxide supported on silica are used at the condensation stage. Total conversion of ethanol and acetaldehyde in these processes is about 35% with the yield of butadiene about 60%. The service cycle of these catalysts is 15-30 hours.

The methods carried out using such heterogeneous catalyst are described, for example, in the following patents: U.S. Pat. Nos. 2,438,464, 2,357,855, 2,447,181, JP 57102822, JP 58059928, GB 573631.

There are methods for production of butadiene which use zirconium and thorium oxides deposited on silica gel (U.S. Pat. No. 2,436,125) or magnesium oxide (U.S. Pat. No. 2,374,433) as the catalyst.

Another approach for production of butadiene is the one-stage conversion of ethanol over solid catalysts at high temperature. In this method, acetaldehyde required for the reaction is formed directly on the catalyst in situ, hence increasing the selectivity of the process and reducing the yield of undesirable by-products. Total conversion of ethanol and acetaldehyde in the process achieves 30-70% with the yield of butadiene of about 45-70%. The service cycle of the said catalysts is 10-100 hours.

The methods carried out usingdescribed above heterogeneous catalysts are disclosed, for example, in the following patents: GB331402, GB331482, FR665917, WO 2014180778 A1, WO 2014199348 A3, EP 3090801 A1. In general, in these patents the catalysts based on two components are used: one component is a metal in a zero oxidation state, preferably copper, silver and gold, and the another is oxide of transition metal, preferably of zirconium, magnesium, tantalum, or zinc.

Conversion of ethanol to butadiene was studied in "Makshina, W. Janssens, B. F. Sels, P. A. Jacobs, "Catalytic study of the conversion of ethanol into 1,3-butadiene", Catalysis Today, 198 (2012) 338-344". In this study, a catalyst based on mixed silicon and aluminum oxide, with the addition of individual transition metals or their oxides was used.

There is a method for conversion of ethanol in the gaseous phase over the solid catalyst comprising of a metal selected from the group of silver, gold or copper, and a metal oxide selected from the group of magnesium, titanium, zirconium or tantalum oxides. The temperature of the process is 200-400° C., atmospheric pressure and WHSV of 0.1-15 g/g·h(RU Patent No. 2440962).

There is a catalyst comprising of metals selected from the III, IV, and V groups of the periodic system of elements, preferably hafnium, zirconium, zinc tantalum and niobium, supported on a mesoporous silicon oxide (KR 2014/050 531 A). However, despite the large surface area of the support, this method has the same disadvantages as its prototype (RU 2440962).

Disadvantage of all the listed above methods utilizing oxide catalysts and supported oxide catalysts is a low yield of butadiene due to the use of bulk oxides and/or non-uniform distribution of active metals and oxides on the surface of the catalysts.

There are known methods for production of butadiene from ethanol over catalysts, which use BEA type zeolites with isomorphically substituted zirconium, tantalum and niobium atoms obtained by hydrothermal or post-synthetic modification as an oxide component.

Conversion of ethanol to butadiene was studied in the following papers:"P I Kyriienko, O V Larina, S O Soloviev, S M Orlyk, S Dzwigaj, High selectivity of TaSiBEA zeolite catalysts in 1,3-butadiene production from ethanol and acetaldehyde mixture, Catalysis Communication, 77 (2016) 123-126", "P I Kyriienko, O V Larina, S O Soloviev, S M Orlyk, C Calers, S Dzwigaj, Ethanol Conversion into 1,3-Butadiene by the Lebedev Method over MTaSiBEA Zeolites (M=Ag, Cu, Zn), ACS Sustainable Chemistry and Engineering, 5 (2017) 2075-2083", "P I Kyriienko, O V Larina, N. Popovych, S O Soloviev, Y. Millot, S Dzwigaj, Effect of the niobium state on the properties of NbSiBEA as bifunctional catalysts for gas- and liquid-phase tandem processes, Journal of Molecular Catalysis A: Chemical, 424 (2016) 27-36", "V L Sushkevich, II Ivanova, Ag-Promoted ZrBEA Zeolites Obtained by Post-Synthetic Modification for Conversion of Ethanol to Butadiene, ChemSusChem, 9 (2016) 2216-2225". In these studies, the catalysts based on a zeolite with BEA type structure post-synthetically modified with tantalum, zirconium or niobium, and with the subsequent addition of metals selected from silver, copper and zinc, were used.

The closest by technical essence is a method of butadiene synthesis from ethanol over zirconium containing BEA type zeolite catalyst, synthesized via hydrothermal process and modified with silver (V L Sushkevich, II Ivanova, E Taarning, Ethanol conversion into butadiene over Zr-containing molecular sieves doped with silver, Green Chemistry, 17 (2015) 2552-2559). However, the small pore size of the zeolite material hinders desorption of the reaction products, as well as the coke precursors, leading to the fast deactivation of the catalyst.

The disadvantages of the known methods, including the prototype, are the low selectivity of the ethanol conversion towards butadiene due to the presence of strong acid sites that are responsible for the side reactions of ethanol dehydration to ethylene and diethyl ether, high regeneration temperature, rapid deactivation of the catalyst. Moreover, the high price of metals and oxides used in the preparation of the catalyst requires high catalyst stability and long catalyst lifetime.

SUMMARY OF THE INVENTION

The goal of the present invention is development of one-stage process for synthesis of butadiene from ethanol and mixtures of ethanol with acetaldehyde, over the catalyst capable for achieving high and stable butadiene yield along with high selectivity to butadiene over multiple synthesis-regeneration cycles.

This aim can be achieved using the described method of conversion of ethanol to butadiene in the gas phase in the presence of the mesoporous zeolite catalyst with a BEA type structure having a molar composition of the framework of ZrO2 (20-1000)SiO2 and comprising of at least one metal in the zero oxidation state, preferably, silver, copper and gold or combinations of thereof It is possible to use the catalyst modified with an alkali metals, preferably, lithium, sodium, potassium, rubidium or cesium or combination of thereof.

It is possible to use a catalyst with silica or alumina binder.

The process is carried out in the gas-phase, preferably at 200-400° C., at the atmospheric pressure and feed rate of 0.1-15 g/g·h.

The weight ratio of acetaldehyde to ethanol in a mixture can be (0-3):10.

Preferably the process is carried out in of continuous flow in a fixed bed reactor.

Regeneration of the catalyst is possible at the temperature of 350-650° C. in an oxygen-containing gas stream with the repeated use of the catalyst for synthesis of butadiene while maintaining the initial activity, selectivity and durability parameters.

The result of the method in the scope of claim 1 is the high yield and selectivity to butadiene with high stability of the catalyst during the reaction and after regeneration.

This result is achieved by designing the catalysts with the structure that provides free access of the reagents and reaction products to the active sites and protects the outer surface of the zeolite crystals from accumulation of heavy products. Facilitation of the mass transfer of the molecules of reagents to the active sites of the zeolite located inside the zeolite channels and the mass transfer of the reaction products from the reaction zone gives a possibility to obtain high yields of the target product, butadiene. This leads to the decrease of formation of by-products and coke precursors and to an increase of the rate of regeneration with the coherent decrease of the regeneration temperature.

DETAILED DESCRIPTION OF THE INVENTION

In general, the claimed method for production of butadiene is carried out as follows.

Pre-treatment of the catalyst is carried out by its heating up to 300-500° C. in a flow of inert gas (nitrogen) with ramp rate of 500 C/h and dwelling at this temperature for 30 minutes, then the reactor is cooled to the reaction temperature, and the catalyst is reduced in a flow of hydrogen for 30 minutes. Ethanol or a mixture of ethanol and acetaldehyde are fed to the fixed-bed reactor. At the reactor outlet, the obtained products are separated into liquid and gaseous products. The composition of products is determined using gas chromatography. After the reaction, the adsorbed products and reagents are removed by purging with a flow of inert gas and regeneration is carried out in oxygen containing gas. Then the synthesis of butadiene is repeated, starting from the pre-treatment in a flow of dry inert gas at the temperature of 300-500° C.

Conversion and yield of the target product are calculated as follows:

$$\text{Conversion (\%)} = n_{but}/(n_{acet.inc.} + n_{ethan.inc.}) \cdot 200;$$

$$\text{Yield (\%)} = n_{but}/(n_{acet.tr.} + n_{ethan.tr.}) \cdot 200;$$

where $n_{but}$—is a flow of butadiene, mol/hr;
$n_{acet.inc.}$, $n_{ethan.inc.}$—is a flow of incoming acetaldehyde and ethanol, mol/hr;
$n_{acet.conv.}$, $n_{ethan.conv.}$—is a flow of converted acetaldehyde and ethanol, mol/hr.

Mesoporous Zr-containing zeolites with a BEA type structure used in the claimed method can be prepared according to the following procedures.

1st method: Zr-containing BEA type zeolite (ZrBEA) is obtained by hydrothermal crystallization of the 1.0 SiO$_2$: 0.005-0.01 ZrO$_2$: 0.56 TEAOH: 6H$_2$O: 0.56 HF composition gel, where TEA is a tetraethylammonium cation, at 140° C. for 10 days. The zeolite obtained after crystallization is washed with water, dried at 100° C. and calcined at 550° C. for 6 hours. Formation of mesopores is carried out by desilylation of the obtained ZrBEA zeolite by treatment for 2-24 h in 0.2-0.7 M alkaline solution (NaOH, KOH or similar water-soluble base) at room temperature. As a result of the treatment, a mesoporous zeolite catalyst is obtained which retains crystalline structure of the original microporous crystalline silicate.

2nd method: Desilylated samples of BEA type zeolite are prepared by stirring of highly crystalline aluminosilicates having BEA type zeolite structure in 0.1-0.7 M alkaline solution (NaOH, KOH or similar water-soluble base) for 3-24 hours at room temperature. The obtained desilylated mesoporous zeolites (deSiAl-BEA) are dealuminated in a solution of nitric acid (70 wt %) at 80° C. for 12 hours until complete removal of aluminium. The resulting zeolite is treated in the solution of ZrOCl$_2$ in dimethylsulfoxide at the temperature of 130° C. for 12 hours, which leads to the incorporation of Zr atoms into the zeolite framework. As the result, Zr-containing mesoporous zeolite Zr-(BEA) is obtained.

At the last stage, metals selected from the group of silver, copper, gold are introduced into the mesoporous zeolite catalyst with a BEA type structure obtained by 1st and 2nd methods.

The important feature of the mesoporous catalysts with a BEA type structure is the presence of two types of pores-micropores, which represent 60-90% of the total pore volume of zeolite, and mesopores formed in the desilylation process, which represent 10-40% of the total pore volume accordingly).

The following examples illustrate the invention and the obtained result in comparison with known methods for production of butadiene and do not limit the invention.

Example 1

20.8 g of tetraethyl orthosilicate are mixed with 11.8 g of tetraethylammonium hydroxide and 7.8 g of water for the hydrolysis at 50° C. with gradual removal of forming ethanol. Then, 0.13 g of zirconyl chloride and 5 g of a 40% aqueous solution of hydrofluoric acid are added with stirring. The resulting gel is transferred to a Teflon-line autoclave and crystallization is carried out at 140° C. for 5 days. The zeolite obtained after crystallization is washed with water, dried at 100° C. and calcined at 550° C. for 6 hours.

20 g of the microporous crystalline silicate with BEA type structure SiO2/ZrO2=200 obtained at the previous step are added to 120 ml of a 0.5 mol/L NaOH solution. The resulting suspension is stirred at room temperature for 0.5 hours. After the alkaline treatment, the material is filtered, washed with distilled water, dried at 100° C. for 24 hours, calcined at 550° C. for 24 hours. As the result, the mesoporous catalyst having a BEA type zeolite structure with the pore volume of 0.226 cm$^3$/g, and the fraction of micropores and mesopores of 0.74 and 0.26, respectively, is synthesized. Then, the catalyst is impregnated according to its wetness capacity with an aqueous solution of silver nitrate until a silver concentration becomes 1% by weight (in terms of metal), dried and calcined at 500° C.

The resulting catalyst, having a 2Ag-1.5ZrO2-200SiO2 composition, is placed into the reactor, purged with nitrogen at 500° C. for 1 hour, then the temperature is decreased to 320° C. and the catalyst is purged with hydrogen for 0.5 hours. Then the gas flow is switched to nitrogen (10 ml/min) and ethanol is fed with the rate of 1.2 g/hr. The reaction is carried out for 3 hours. At the reactor outlet butadiene with an ethanol conversion of 42% and a yield of butadiene on the converted ethanol of 73% is obtained.

Unreacted ethanol is recycled. The results of the experiment are presented in Table 1.

Example 2

The process is carried out as described in the example 1 with process parameters measured after 100 hours in the stream. Parameters of the process are shown in Table 1.

Example 3 (Comparative)

The process is carried out as described in the example 1 with the catalyst based on zirconium oxide and silver supported on silica gel I and synthesized is according to the RU 2440962 prototype. Parameters of the process are shown in Table 1.

Example 4 (Comparative)

The process is carried out as described in the example 3 with the process parameters measured after 100 hours in the stream. Parameters of the process are shown in Table 1.

The analysis of the results obtained in examples 1-4 shows the advantages of the proposed method for production of butadiene from ethanol in comparison with the known methods. High conversion and yield of butadiene are not provided when using the known catalysts. High ethanol conversion, high butadiene yield and high stability of catalyst are achieved when catalysts containing mesoporous zeolite materials and the declared metals are used.

Example 5

20 g of zeolite BEA type with SiO$_2$/Al$_2$O$_3$=75 are added to 120 ml of 0.7 mol/L solution of NaOH. The obtained suspension is stirred at room temperature for 0.5 hours. Then, the material is filtered, washed with distilled water, dried at 100° C. for 24 hours, calcined at 550° C. for 24 hours. As the result, a mesoporous catalyst having a BEA type zeolite structure is obtained with the pore volume of 0.45 cm$^3$/g, and the micropores and mesopores-fraction of 0.60 and 0.40, respectively.

10 g of the obtained desilylated microporous crystalline aluminosilicate having BEA type structure with SiO2/Al$_2$O$_3$=3000 are added to 250 ml of nitric acid (65 wt %).

The obtained mixture is heated at 80° C. for 12 hours. The obtained dealuminated zeolite is filtered, washed by water and dried.

5 g of the obtained mesoporous dealuminated zeolite BEA type with SiO2/Al2O3=3000 are added to a solution of 20 g of ZrOC12 in 200 ml of dimethyl sulfoxide. The mixture is heated at 130° C. for 12 hours. Then the catalyst is filtered, washed with water, dried and calcined at a temperature of 500° C. that the resulting powder is impregnated according to its wetness capacity with an aqueous solution of silver nitrate to achieve silver loading of 1 wt %, dried and calcined at 500° C.

Testing of the obtained catalyst having 30Ag-70ZrO$_2$—Al$_2$O$_3$-3000SiO$_2$ composition is carried out as described in the example 1.

Example 6

The process is carried out as described in the example 1 over the catalyst doped with sodium corresponding to the composition of 30Ag-70ZrO$_2$—Al$_2$O$_3$-5Na$_2$O-3000SiO$_2$. The process is carried out with the addition of acetaldehyde into the feed with the ratio acetaldehyde/ethanol=1/10. Parameters of the process are shown in Table 1.

in further examples, a possibility to carry out the processes with different catalysts from the declared under different process conditions is shown.

Example 7

The process is carried out as described in the example 1 over the catalyst containing copper instead of silver and addition of acetaldehyde into the feed with the ratio acetaldehyde/ethanol 1/10. Parameters of the process are shown in Table 1.

Example 8

The process is carried out as described in the example 5 over the catalyst containing gold instead of copper. Parameters of the process are shown in Table 1.

Example 9

The process is carried out as described in the example 1 with the addition of acetaldehyde with the ratio acetaldehyde/ethanol=1/10. Parameters of the process are shown in Table 1.

Examples 10-14 illustrate the possibility to use the method for production of butadiene in a wide range of process conditions.

Example 15

The process is carried out as described in the example 1 over the catalyst with a binder (aluminum oxide). Parameters of the process are shown in Table 1.

Example 16

The process is carried out as shown in the example 1 over the catalyst with a binder (silicon oxide). Parameters of the process are shown in Table 1.

Example 17

The process is carried out as described in the example 9 over the catalyst regenerated in a flow of air at 450° C. Parameters of the process are shown in Table 1.

Thus, the presented above examples show the production of butadiene in one step process achieving high ethanol conversion and high yield of butadiene with the stable operation of the catalyst.

Although this invention has been described in detail in the examples under preferred conditions, these examples of the invention are provided only for illustrative purposes. This description should not be regarded as limiting the scope of the invention, since changes not going beyond the scope of the formula of invention and directed to the adaptation to specific conditions or situations can be made to the described process stages. Variations and modifications, including equivalent solutions, defined by the claims are possible within the scope of the invention.

comprising 10-40% of the total pore volume of the mesoporous Zr-containing zeolite, and at least one metal in a zero oxidation state selected from the group consisting of silver, copper, gold, and combinations of thereof.

2. The method according to claim 1 further comprising the step of preparing, the mesoporous Zr-containing zeolite by desilylation in an alkaline aqueous solution containing 0.1-0.7 mol/L of a water-soluble base.

3. The method according to claim 1 further comprising the step of preparing the mesoporous Zr-containing zeolite by a direct hydrothermal synthesis or by a post-synthetic modification of the aluminum-containing BEA zeolite to introduce Zr into a mesoporous zeolite.

TABLE 1

| No of the example | Composition of the catalyst (by weight) | Conditions | | | | Results | |
|---|---|---|---|---|---|---|---|
| | | Temperature °C. | Weight hourly space velocity, g/g · h | Acetaldehyde/ ethanol | Duration of the experiment, h | Conversion, % | Yield of butadiene in terms of the converted reagents, mol. % |
| 1. | $2Ag-1,5ZrO_2-200SiO_2$ | 320 | 0.3 | 0 | 3 | 42 | 73 |
| 2 | $2Ag-1,5ZrO_2-200SiO_2$ | 320 | 0.3 | 0 | 100 | 42 | 73 |
| 3 | $1Ag-12ZrO_2-300SiO_2$ | 320 | 0.3 | 0 | 3 | 34 | 72 |
| 4 | $1Ag-12ZrO_2-300SiO_2$ | 320 | 0.3 | 0 | 100 | 29 | 71 |
| 5 | $30Ag-70ZrO_2-Al_2O_3-3000SiO_2$ | 320 | 0.3 | 0 | 3 | 66 | 56 |
| 6 | $30Ag-70ZrO_2-Al_2O_3-5Na_2O-3000SiO_2$ | 320 | 0.3 | 0 | 3 | 52 | 75 |
| 7 | $2Cu-1,5ZrO_2-200SiO_2$ | 320 | 0.3 | 1/10 | 3 | 69 | 34 |
| 8 | $2Au-1,5ZrO_2-200SiO_2$ | 320 | 0.3 | 1/10 | 3 | 46 | 73 |
| 9 | $2Ag-1,5ZrO_2-200SiO_2$ | 320 | 0.3 | 1/10 | 3 | 53 | 73 |
| 10 | $2Ag-1,5ZrO_2-200SiO_2$ | 200 | 0.3 | 1/10 | 3 | 5 | 55 |
| 11 | $2Ag-1,5ZrO_2-200SiO_2$ | 400 | 0.3 | 1/10 | 3 | 98 | 35 |
| 12 | $2Ag-1,5ZrO_2-200SiO_2$ | 320 | 0.1 | 1/10 | 3 | 78 | 60 |
| 13 | $2Ag-1,5ZrO_2-200SiO_2$ | 320 | 15 | 1/10 | 3 | 14 | 64 |
| 14 | $2Ag-1,5ZrO_2-200SiO_2$ | 320 | 0.3 | 3/10 | 3 | 75 | 55 |
| 15 | $2Ag-1,5ZrO_2-100Al_2O_3-200SiO_2$ | 320 | 0.3 | 1/10 | 3 | 100 | 2 |
| 16 | $2Ag-1,5ZrO_2-300SiO_2$ | 320 | 0.3 | 1/10 | 3 | 48 | 72 |
| 17 | $2Ag-1,5ZrO_2-200SiO_2$ | 320 | 0.3 | 1/10 | 3 | 53 | 73 |

The invention claimed is:

1. A one-stage method for production of butadiene, the method comprising the step of reacting ethanol or a mixture of ethanol with acetaldehyde in a gaseous phase in a presence of a solid phase catalyst, wherein the solid phase catalyst comprises a mesoporous Zr-containing zeolite having a BEA structure, the mesoporous Zr-containing zeolite containing micropores comprising 60-90% of a total pore volume of the mesoporous Zr-containing zeolite, mesopores comprising 10-40% of the total pore volume of the mesoporous Zr-containing zeolite, and at least one metal in a zero oxidation state selected from the group consisting of silver, copper, gold, and combinations of thereof.

4. The method according to claim 1, wherein the mesoporous Zr-containing zeolite is modified by at least one alkali metal.

5. The method according to claim 1, wherein the solid phase catalyst comprises a binder selected from the group consisting of silicon oxide and aluminum oxide.

6. The method according to claim 1, wherein said reacting is carried out in conditions of gas-phase condensation at 200-400° C. under atmospheric pressure and a feed rate of 0.1-15 g/g·h.

7. The method according to claim 1, wherein said reacting is carried out in a presence of acetaldehyde and at a weight ratio of acetaldehyde to ethanol in a mixture of up to 3:10.

* * * * *